US010201396B2

(12) United States Patent
Rosenbaum et al.

(10) Patent No.: US 10,201,396 B2
(45) Date of Patent: Feb. 12, 2019

(54) TROCAR ASSEMBLY WITH A CLEANING ELEMENT FOR USE DURING A LAPAROSCOPIC PROCEDURE

(71) Applicant: CareFusion 2200, Inc., San Diego, CA (US)

(72) Inventors: Joanna L. Rosenbaum, Evanston, IL (US); Jeanny Chung, Deerfield, IL (US); Patrick Hubbard, Vernon Hills, IL (US); Joseph Prybell, Mundelein, IL (US); Corrie Threlkeld, Vernon Hills, IL (US); Sara Tillman, Vernon Hills, IL (US); Brandon Toth, Vernon Hills, IL (US); Andrew P. VanDeWeghe, Grayslake, IL (US); Thomas Wilschke, Chicago, IL (US); Jesse Charles Darley, Madison, WI (US); Christopher Alan Harris, Madison, WI (US); Curtis B. Irwin, Madison, WI (US); Stephen A. Latham, Sun Prairie, WI (US); Daniel J. Lee, Princeton Junction, NJ (US); Douglas Rodenkirch, Sun Prairie, WI (US); Jeffrey R. Staszak, Deerfield, WI (US)

(73) Assignee: Carefusion 2200, Inc., San Diego, CA (US)

( * ) Notice: Subject to any disclaimer, the term of this patent is extended or adjusted under 35 U.S.C. 154(b) by 0 days.

(21) Appl. No.: 15/452,169

(22) Filed: Mar. 7, 2017

(65) Prior Publication Data
US 2018/0256283 A1 Sep. 13, 2018

(51) Int. Cl.
*A61B 90/70* (2016.01)
*A61B 1/00* (2006.01)
(Continued)

(52) U.S. Cl.
CPC .......... *A61B 90/70* (2016.02); *A61B 1/00154* (2013.01); *A61B 1/122* (2013.01);
(Continued)

(58) Field of Classification Search
CPC ..... A61B 90/70; A61B 1/00154; A61B 1/122; A61B 1/3132; A61B 17/0218;
(Continued)

(56) References Cited

U.S. PATENT DOCUMENTS

| 5,274,874 A | 1/1994 | Cercone et al. |
| 5,351,675 A | 10/1994 | Brodsky |

(Continued)

FOREIGN PATENT DOCUMENTS

| EP | 2111782 A2 | 10/2009 |
| EP | 2111808 A2 | 10/2009 |

(Continued)

OTHER PUBLICATIONS

International Search Report and Written Opinion in Application No. PCT/US2018/020850, dated May 17, 2018, 12 pages.
(Continued)

*Primary Examiner* — Pedro Philogene
*Assistant Examiner* — David C Comstock
(74) *Attorney, Agent, or Firm* — Dinsmore & Shohl LLP

(57) ABSTRACT

The present disclosure relates to a trocar assembly with an integrated scope-cleaning structure. The trocar assembly may include a chamber with a proximal opening configured to receive a distal end of a scope. A cannula extend distally from the chamber and may be configured to extend distally into a patient body. The cannula may be further configured to receive the distal end of the scope such that the scope can be maneuvered through the cannula to a location within the patient body. The trocar assembly may include a cleaning element forming a surface within the chamber, where the
(Continued)

surface of the cleaning element is configured to remove debris from at least one non-longitudinal, end-facing surface of the scope.

20 Claims, 12 Drawing Sheets

(51) Int. Cl.
    *A61B 1/12*         (2006.01)
    *A61B 1/313*       (2006.01)
    *A61B 17/02*       (2006.01)
    *A61B 17/34*       (2006.01)
    *A61B 17/00*       (2006.01)

(52) U.S. Cl.
    CPC ........ *A61B 1/3132* (2013.01); *A61B 17/0218* (2013.01); *A61B 17/3423* (2013.01); *A61B 2017/00367* (2013.01); *A61B 2090/701* (2016.02)

(58) Field of Classification Search
    CPC .......... A61B 17/3423; A61B 2090/701; A61B 2017/00367
    USPC ................ 600/204, 206, 184, 188, 127, 157
    See application file for complete search history.

(56) References Cited

U.S. PATENT DOCUMENTS

| | | | |
|---|---|---|---|
| 5,365,267 A | | 11/1994 | Edwards |
| 5,382,297 A | | 1/1995 | Valentine et al. |
| 5,549,543 A | | 8/1996 | Kim |
| 5,643,227 A | | 7/1997 | Stevens |
| 5,651,757 A | | 7/1997 | Meckstroth |
| 5,842,971 A | | 12/1998 | Yoon |
| 5,880,779 A | | 3/1999 | Rhynes |
| 5,910,106 A | | 6/1999 | Morgan et al. |
| 5,916,145 A | | 6/1999 | Chu et al. |
| 5,980,493 A | | 11/1999 | Smith et al. |
| 6,197,041 B1 | | 3/2001 | Schichman et al. |
| 6,319,266 B1 | | 11/2001 | Stellon et al. |
| 6,482,181 B1 | | 11/2002 | Racenet et al. |
| 6,497,716 B1 | | 12/2002 | Green et al. |
| 6,685,630 B2 | | 2/2004 | Sauer et al. |
| 6,976,957 B1 | * | 12/2005 | Chin ...................... A61B 1/313 600/157 |
| 6,981,966 B2 | | 1/2006 | Green et al. |
| 7,025,747 B2 | | 4/2006 | Smith |
| 7,294,136 B2 | | 11/2007 | Dubrui et al. |
| 7,367,960 B2 | | 5/2008 | Stellon et al. |
| 7,390,315 B2 | | 6/2008 | Stellon et al. |
| 7,537,563 B2 | | 5/2009 | Temple |
| 7,691,089 B2 | | 4/2010 | Gresham |
| 7,771,384 B2 | | 8/2010 | Ravo |
| 7,811,225 B2 | | 10/2010 | Sauer et al. |
| 7,811,251 B2 | | 10/2010 | Wenchell et al. |
| 7,988,670 B2 | | 8/2011 | Smith |
| 8,070,730 B2 | | 12/2011 | Rockrohr |
| 8,092,423 B2 | | 1/2012 | Gresham |
| 8,123,682 B2 | | 2/2012 | Wenchell et al. |
| 8,152,717 B2 | | 4/2012 | Gomez |
| 8,202,290 B2 | | 6/2012 | Smith |
| 8,206,411 B2 | | 6/2012 | Thompson et al. |
| 8,211,135 B2 | | 7/2012 | Heinrich et al. |
| 8,223,193 B2 | | 7/2012 | Zhao et al. |
| 8,241,251 B2 | | 8/2012 | Gresham |
| 8,257,253 B2 | | 9/2012 | Piskun |
| 8,257,254 B2 | | 9/2012 | Piskun |
| 8,257,315 B2 | | 9/2012 | Franer et al. |
| 8,267,896 B2 | * | 9/2012 | Hartoumbekis ........ A61B 1/126 604/167.01 |
| 8,394,018 B2 | | 3/2013 | Piskun |
| 8,449,460 B2 | | 5/2013 | Duke et al. |
| 8,458,971 B2 | | 7/2013 | Smith et al. |
| 8,491,545 B2 | | 7/2013 | Shelton, IV |
| 8,496,622 B2 | | 7/2013 | Shelton, IV |
| 8,535,220 B2 | | 9/2013 | Mondschein |
| D700,326 S | | 2/2014 | Minnelli et al. |
| 8,708,889 B2 | | 4/2014 | Feuer et al. |
| 8,726,037 B2 | | 5/2014 | Franer |
| 8,728,109 B2 | | 5/2014 | Piskun |
| 8,764,648 B2 | | 7/2014 | Piskun |
| 8,771,307 B2 | | 7/2014 | Franer |
| 8,870,747 B2 | | 10/2014 | Moreno, Jr. et al. |
| 8,911,463 B2 | | 12/2014 | Fischvogt |
| 8,932,249 B2 | | 1/2015 | Parihar et al. |
| 8,961,552 B2 | | 2/2015 | Fischvogt et al. |
| 8,968,250 B2 | | 3/2015 | McGinley et al. |
| 9,039,604 B2 | | 5/2015 | Yoshida |
| 9,078,562 B2 | | 7/2015 | Poll et al. |
| D736,926 S | | 8/2015 | Minnelli et al. |
| 9,211,059 B2 | | 12/2015 | Drach et al. |
| 9,265,899 B2 | | 2/2016 | Albrecht et al. |
| 9,289,115 B2 | | 3/2016 | Dang et al. |
| D753,303 S | | 4/2016 | Dannaher |
| 9,314,266 B2 | | 4/2016 | Kahle et al. |
| 9,314,267 B2 | | 4/2016 | Piskun et al. |
| 9,358,040 B2 | | 6/2016 | Kahle et al. |
| 2002/0022762 A1 | | 2/2002 | Beane et al. |
| 2005/0043683 A1 | | 2/2005 | Ravo |
| 2006/0293559 A1 | * | 12/2006 | Grice, III ........... A61B 1/00135 600/102 |
| 2008/0194915 A1 | | 8/2008 | Blackhurst et al. |
| 2008/0200765 A1 | | 8/2008 | Mondschein |
| 2009/0112057 A1 | | 4/2009 | Kammer et al. |
| 2009/0240111 A1 | * | 9/2009 | Kessler .............. A61B 1/00032 600/155 |
| 2009/0270686 A1 | | 10/2009 | Duke et al. |
| 2010/0012152 A1 | | 1/2010 | Hansen |
| 2011/0149057 A1 | | 6/2011 | Beck et al. |
| 2012/0101337 A1 | | 4/2012 | Clark et al. |
| 2012/0187104 A1 | | 7/2012 | Heymann et al. |
| 2013/0041230 A1 | | 2/2013 | Hartoumbekis et al. |
| 2013/0053639 A1 | * | 2/2013 | Ihde, II ................... A61B 1/04 600/109 |
| 2013/0085329 A1 | | 4/2013 | Morrissette et al. |
| 2013/0102843 A1 | | 4/2013 | Feuer et al. |
| 2013/0150670 A1 | | 6/2013 | O'Prey et al. |
| 2014/0171739 A1 | | 6/2014 | Nguyen |
| 2014/0215736 A1 | * | 8/2014 | Gomez ............... A61B 1/00154 15/104.05 |
| 2014/0235944 A1 | | 8/2014 | Feuer et al. |
| 2014/0249370 A1 | * | 9/2014 | Hurst .................... A61B 1/126 600/114 |
| 2016/0015573 A1 | * | 1/2016 | Ihde, II ................. A61B 90/70 604/385.01 |
| 2016/0113484 A1 | | 4/2016 | Nakaguchi |
| 2016/0166135 A1 | | 6/2016 | Fiset |
| 2018/0035988 A1 | * | 2/2018 | Lau .................. A61B 17/00008 |

FOREIGN PATENT DOCUMENTS

| | | |
|---|---|---|
| EP | 2113215 A1 | 11/2009 |
| EP | 2193742 A1 | 6/2010 |
| EP | 2238928 A1 | 10/2010 |
| EP | 2111782 B1 | 8/2016 |
| WO | WO2010/011563 A2 | 7/2009 |
| WO | WO2010/011563 A3 | 7/2009 |
| WO | WO2013/012790 A2 | 7/2012 |
| WO | WO2013/012790 A3 | 7/2012 |
| WO | WO2013/063153 A2 | 5/2013 |
| WO | WO2014/185334 A1 | 5/2014 |

OTHER PUBLICATIONS

International Search Report and Written Opinion in Application No. PCT/US2018/020856, dated May 17, 2018, 15 pages.

(56) References Cited

OTHER PUBLICATIONS

International Search Report and Written Opinion in Application No. PCT/US2018/020853, dated Jun. 18, 2018, 16 pages.

* cited by examiner

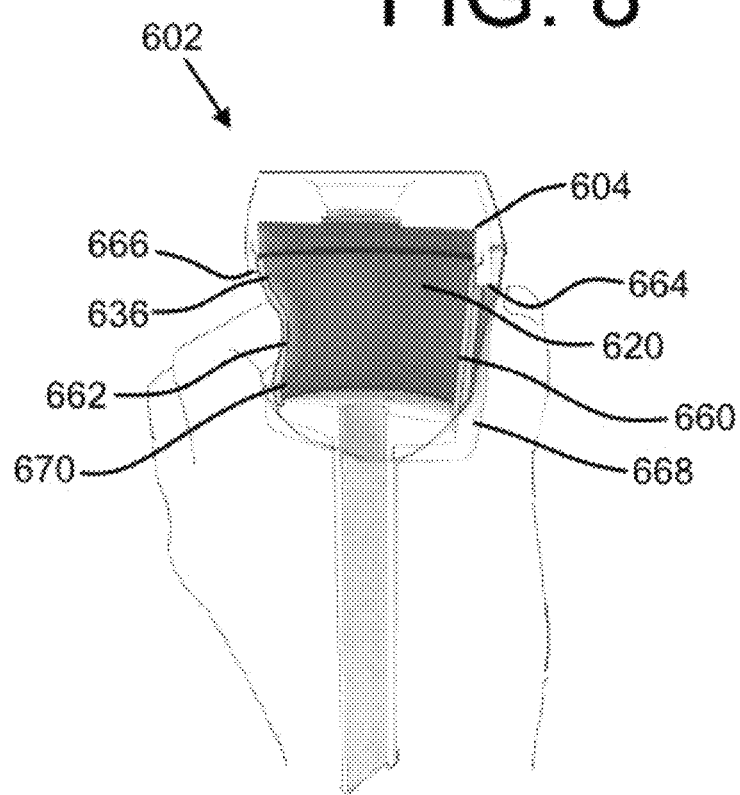

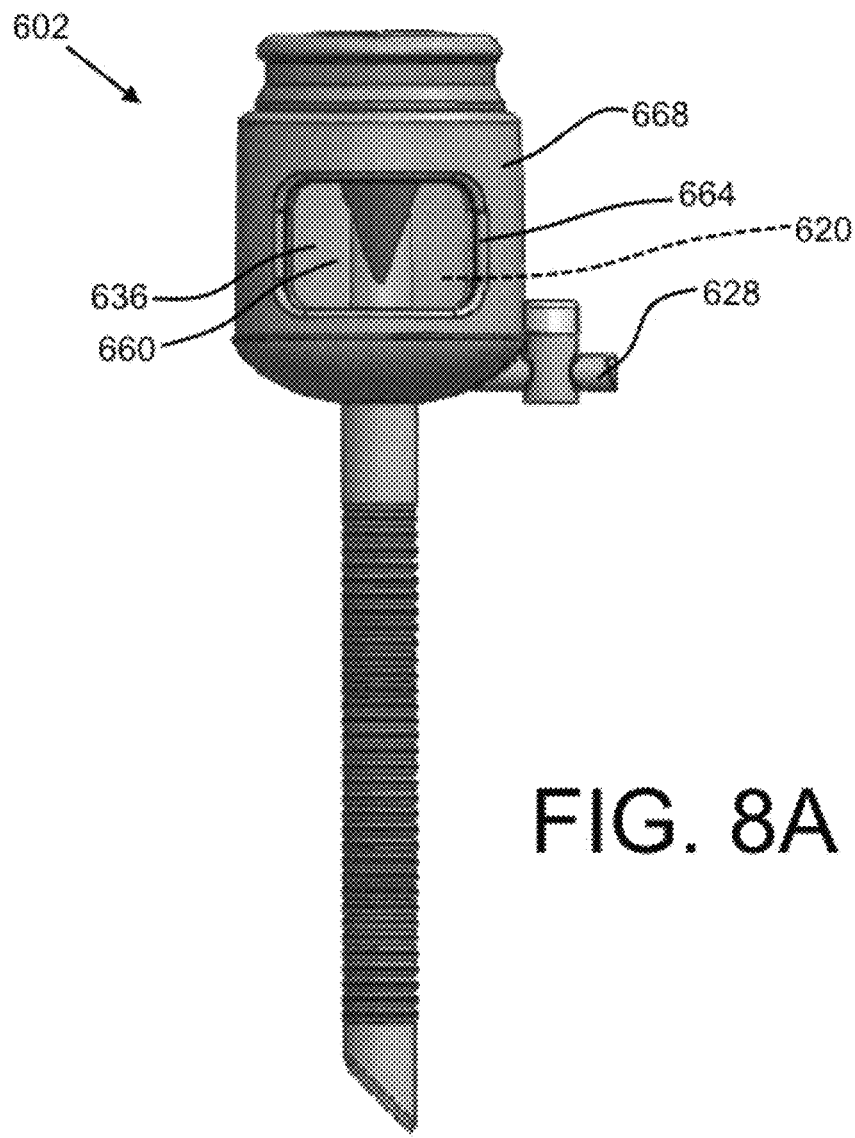

TROCAR ASSEMBLY WITH A CLEANING ELEMENT FOR USE DURING A LAPAROSCOPIC PROCEDURE

FIELD OF TECHNOLOGY

The present disclosure relates generally to trocar assemblies and related devices, and more specifically, to trocar assemblies which can be utilized in laparoscopic medical procedures.

BACKGROUND

Laparoscopic surgery is a minimally-invasive surgical technique typically performed with the assistance of one or more medical instruments inserted through a small incision in a patient's body. Laparoscopic surgery is often preferred to traditional and more invasive surgical procedures because of the reduced frequency and degree of certain postoperative side effects, such as postoperative pain, swelling, internal bleeding, and infection risk. The minimally-invasive nature of laparoscopic procedures may also result in decreased recovery times and shorter hospital stays.

Typical medical devices utilized during laparoscopic procedures have instruments mounted on an elongated metal or plastic body that are inserted into the patient's body and maneuvered to a target area within a body cavity (e.g., the abdominal, pelvic, thoracic, or chest cavity, where insufflation may be used to provide additional space in which to maneuver, which requires a fluid-patent barrier to maintain insufflation pressure in the cavity). One or more trocar assemblies are typically first inserted into the patient body at an incision site (for each), and the instruments access the patient body through the trocar assembly(ies).

Often, a medical device including a camera or other image-transmitting device is inserted through a trocar to transmit one or more images or a live video feed from within the body cavity to a medical professional (such as the surgeon). The device may be referred to as a scope or a laparoscope, and its transmission may guide the medical professional's actions during the laparoscopic procedure.

A problem typically experienced during laparoscopic procures involves a compromised image or video feed due to an obstructed lens of the laparoscope. This obstruction may be caused by condensation (e.g., fog) and/or debris such as bodily fluids or displaced tissue encountered by the lens during the procedure. Such obstruction is problematic because the lens of the laparoscope preferably remains contained in a pressurized and sterile environment (e.g., insufflated body cavity), and removing the lens from that environment for cleaning purposes may cause lengthy interruptions prolonging patient anesthesia and increasing a risk of compromised sterility.

DESCRIPTION

In one aspect, the present disclosure relates to a trocar assembly with an integrated scope-cleaning structure. The trocar assembly may include a chamber with a proximal opening configured to receive a distal end of a scope. A cannula extend distally from the chamber and may be configured to extend distally into a patient body. The cannula may be further configured to receive the distal end of the scope such that the scope can be maneuvered through the cannula to a location within the patient body. The trocar assembly may include a cleaning element receiving surface configured to receiving a cleaning element with a cleaning surface for removing debris from at least one non-longitudinal, end-facing surface of the scope.

The trocar assembly may include a valve configured to form a fluid barrier at or near the proximal opening between an environment within the chamber and an external environment.

A cleaning element may include an opening aligned with a longitudinal axis of the cannula. The surface of the cleaning element may additionally or alternatively include a curved portion.

The cleaning element may be movable with respect to the chamber in response to an input force between a default state and a displaced state. The cleaning element may include an opening, where a longitudinal axis of the cannula extends through the opening when the cleaning element is in a default state, and wherein the cleaning element at least partially obstructs the cannula from a proximal viewpoint when the cleaning element is in a displaced state. A button may be coupled to the cleaning element, where the input force is typically applied to the button, and where the button is movable with respect to the chamber in response to the input force.

At least a portion of the cleaning element may extend along an inner diameter surface of the cannula. The cleaning element may additionally or alternatively include a stepped portion with an edge.

In another aspect, a trocar assembly may include a housing forming a chamber, the chamber having a proximal opening configured to receive a distal end of a scope. A cannula may extend distally along a longitudinal axis from the housing and may be configured to extend distally into a patient body, where the cannula may be further configured to receive the distal end of the scope such that the scope can be maneuvered through the cannula to a location within the patient body. A cleaning element may form a surface within the chamber, and the cleaning element may have an opening aligned with the longitudinal axis of the cannula.

A valve may be configured to form a fluid barrier at the proximal opening between an environment within the chamber and an external environment.

The surface of the cleaning element may include an opening aligned with the longitudinal axis of the cannula when the cleaning surface is received by the cleaning element receiving surface, and may include a curved portion and/or a stepped portion with an edge.

The cleaning element may be movable with respect to the housing in response to an input force between a default state and a displaced state.

The cleaning element may include an opening, where a longitudinal axis of the cannula extends through the opening when the cleaning element is in a default state, and where the cleaning element at least partially obstructs the cannula from a proximal viewpoint when the cleaning element is in a displaced state.

A button may be coupled to the cleaning element, where an input force may be applied to the button, and wherein the button is movable with respect to the chamber in response to the input force In another aspect, the present disclosure related to a cleaning element for cleaning at least one surface of a scope. The cleaning element may include at least one absorbent cleaning surface configured to remove debris from at least one non-longitudinal, end-facing surface of a scope and a second surface configured to secure to a cleaning element receiving surface within a chamber of a trocar assembly. The cleaning surface of the cleaning element may be configured (that is, both sized and shaped) to be fully encompassed within a chamber of a laparoscopy trocar assembly during a cleaning procedure.

The at least one absorbent cleaning surface may include at least one of a concave portion and a stepped portion. At least a portion of the cleaning surface may be displaceable from a default state to a displaced state in response to an input force applied to the cleaning element.

BRIEF DESCRIPTION OF THE DRAWINGS

FIG. 8 shows another embodiment of a trocar assembly with flexible wall portions formed by an inner shell including a cleaning element in accordance with the present disclosure.

FIG. 8A shows a second illustration of the trocar assembly of FIG. 8.

DETAILED DESCRIPTION

Figure 1:
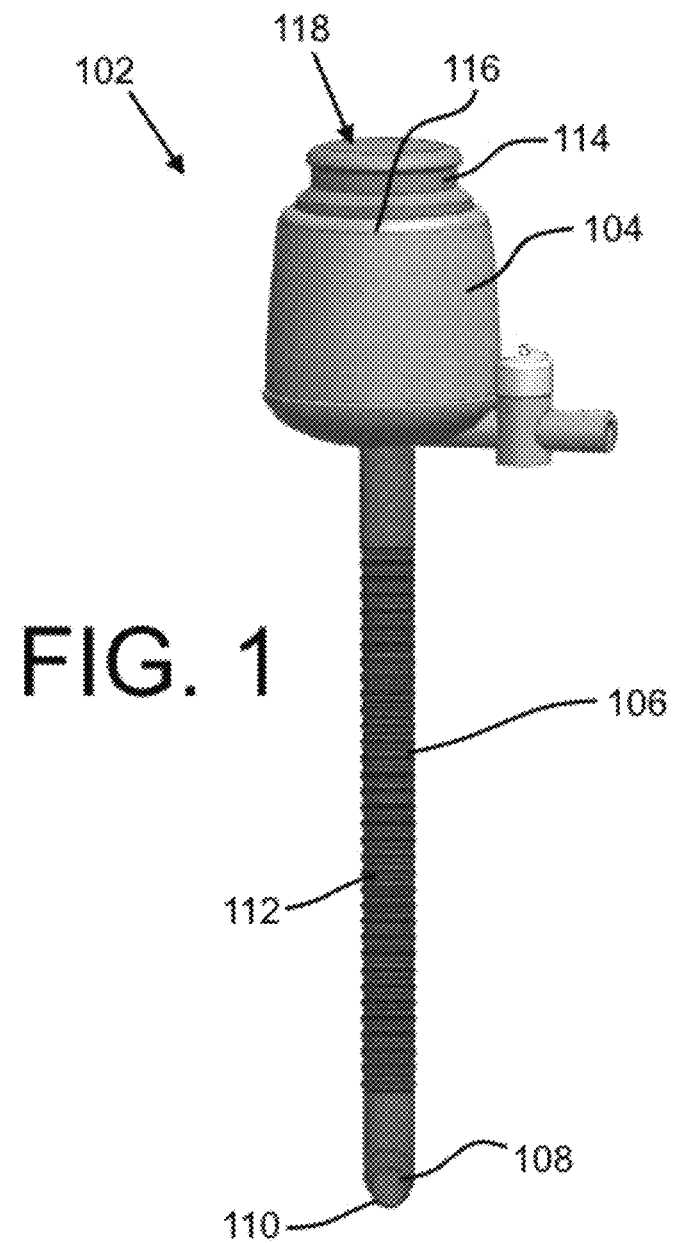
FIG. 1 shows a trocar assembly for use during a laparoscopic procedure in accordance with the present disclosure.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings may or may not be to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry and/or governmental standards (e.g., ASTM, ANSI, IEEE, HIPAA, FDA standards) is defined as complying with the currently published standards as of the original filing date of this disclosure concerning the units, measurements, and testing criteria communicated by those standards unless expressly otherwise defined herein.

The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

FIG. 1 shows a trocar assembly 102 for use during a laparoscopic procedure. The trocar assembly 102 may include a housing 104 with a cannula 106 extending distally from the housing 104. The cannula 106 may include a distal end 108 for placement into a patient body during the laparoscopic procedure. The distal end 108 of the cannula 106 may include a beveled or sharpened end 110 to facilitate entry of the cannula 106 into the patient body. An obturator may additionally or alternatively be included. The cannula 106 may include certain surface characteristics, such as threads or ridges 112, to enhance the stability of the trocar assembly 102 when inserted into a body incision. In some embodiments, a removable bayonet fitting 114 or other suitable securement mechanism may be placed on a proximal side 116 of the housing 104 during deployment of the trocar assembly 102. The bayonet fitting 114 may be configured to secure an obturator to the housing 104 and may provide a surface 118 for receiving an input force from a medical professional intended to direct the cannula 106 into the patient body, for example. The bayonet fitting 114 may be removed once the trocar assembly 102 is deployed.

Figure 2:
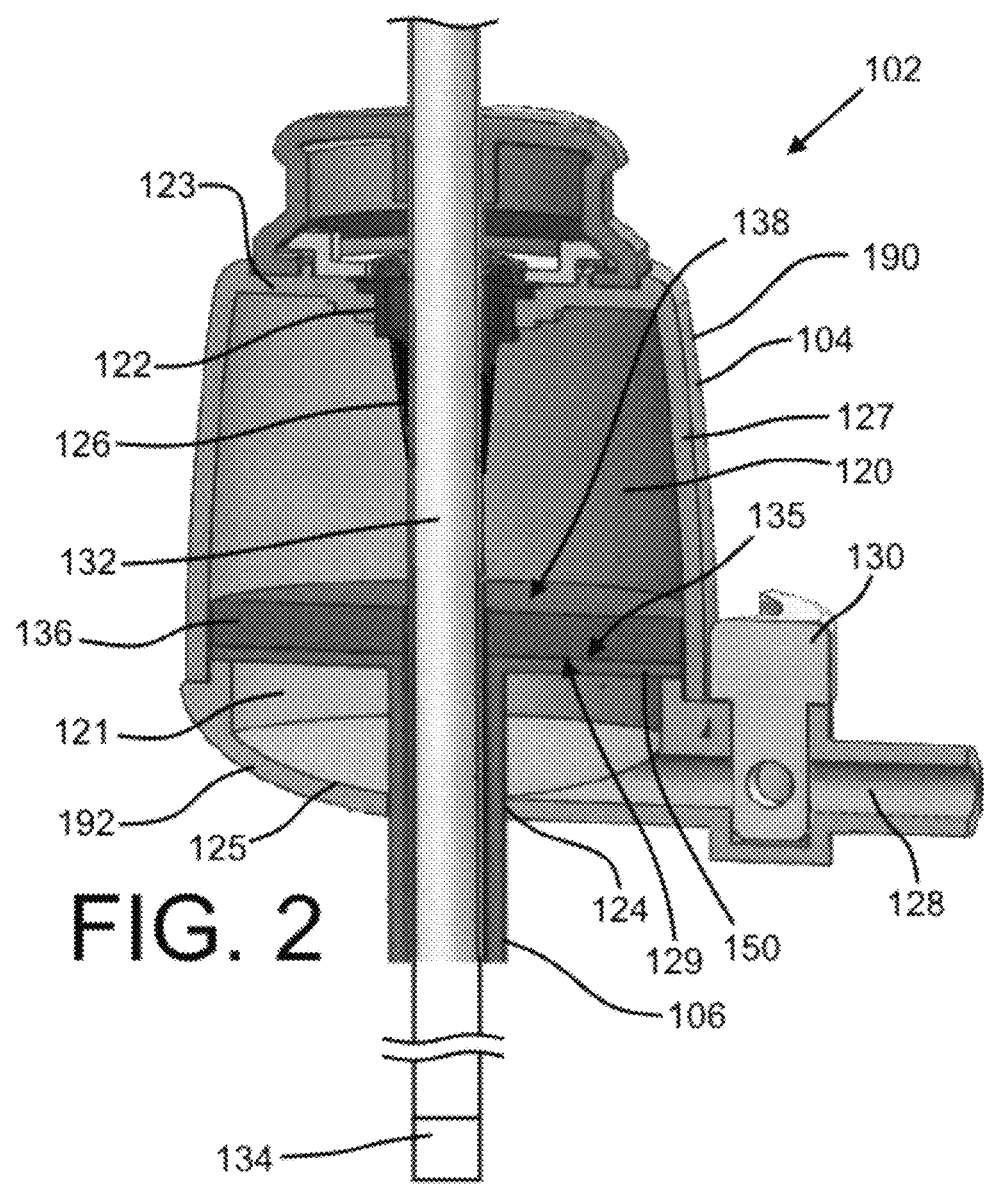
FIG. 2 shows a section view of the trocar assembly of FIG. 1.

FIG. 2 shows a section view of the trocar assembly 102 of FIG. 1. As shown, the cannula 106 may be in fluid communication with a chamber 120 formed by the housing 104. The chamber 120 may be defined by a proximal or top wall 123, a distal or bottom wall 125, and a generally cylindrical side wall 327 extending from the top wall 123 to the bottom wall 125 and defining inner and outer chamber perimeters (i.e., circumferences, when the chamber is rounded but otherwise applicable to any geometry). The chamber 120 may have a proximal opening 122 configured to receive medical devices used during laparoscopic surgery, including but not limited to graspers, dissectors, needles, scissors, clamps, electrodes, forceps, a camera or laparoscope (a "scope"), etc. The proximal opening 122 may be located in a top wall 123 of the housing 104. A valve 126 may be located in the proximal opening 122 and may form a seal or fluid barrier between the chamber 120 and an external environment (e.g., the ambient room environment). Alternatively or in addition, the valve 126 may be located in another location (such as at the opening 124). It may be advantageous for at least one valve 126 to be located at a the proximal opening 122 such that a lens of a scope does not have to pass through the valve 126 prior to cleaning, thereby reducing or eliminating the chance of materials from the valve 126 dirtying the scope's lens. The inner and outer chamber perimeters each is greater than an outer perimeter of the cannula 106.

The chamber 120 may be subjected to a continuous sterile and pressurized environment that extends through the cannula 106 and to the body cavity (herein referred to as the "internal environment" even though the continuous region may extend external of the patient body wall, e.g., within trocar assembly 102). This may be advantageous if maintaining insufflation of the body cavity is desired during all operation—including cleaning—of a trans-trocar-located scope or other device. Further, the controlled environment of the chamber 120 may reduce fogging of a scope by eliminating or reducing temperature changes and/or changes in humidity.

The valve 126 (which may include more than one valve) may include a particular structure that allows certain medical devices to pass through the proximal opening 122 and into the chamber while maintaining the seal or fluid barrier. For example, the valve 126 may include the depicted duckbill seal, an annular seal structure, or both, but other suitable structures may additionally or alternatively be included. The valve 126 may be formed with a compliant material such that it expands or contracts as necessary for compatibility with scopes of different sizes. For example, on the Shore Hardness Scale, the valve 126 may be formed of a material with a hardness between about Shore A 20 to about Shore A 80, such as from about Shore A 30 to about Shore A 60.

An insufflation inlet 128 may communicate with the chamber and may be configured to control the pressure and other characteristics (e.g., temperature, composition of the atmosphere), which may be advantageous for providing precise control of insufflation of a body cavity during the laparoscopic procedure. The insufflation inlet 128 may include an insufflation valve 130, and may be in fluid communication with a pump or other suitable pressure source. As shown, the insufflation inlet 128 may communicate with a distal chamber portion 121 (which is a portion of the chamber 120) that is separated from the remainder of the chamber 120 by a divider 150, and the cleaning element 136 may be located on a proximal face of the divider 150, as shown. Advantageously, the flow of gasses or other contents received into the chamber 120 through the insufflation inlet 128 may be introduced in a manner such that the effect of the flow across cleaning element 136 is reduced or eliminated. For example, when the cleaning element 136 (which is described in detail below) is wetted with a cleaning fluid, concerns of increased evaporation due to fluid flow over the cleaning element 136 may be alleviated.

The trocar assembly 102 may provide an entry or point of access into the body for a scope 132. In non-limiting embodiments, the scope 132 may include a commercially-available rigid laparoscope with a 5 mm or a 10 mm diameter (or any other suitable diameter) with either a non-angled lens or an angled lens, which may be angled at 30 degrees, 45 degrees, 50 degrees, etc. with respect to the longitudinal axis of the scope 132. At least a distal end 134 of the scope 132 may include one or more elements designed to magnify, reflect, illuminate, and/or capture images of internal body areas under treatment, and then transmit those images back to the medical professional controlling the procedure (herein referred to as a "viewing element"). The scope 132 may be inserted into proximal opening 122 of the chamber 120, may extend through the chamber 120, and may extend through into the cannula 106 through a distal opening 124 in the bottom wall 125 of the chamber 120, where the distal opening 124 is in fluid and mechanical communication with the cannula 106. The scope 132 may further extend distally to the cannula's distal end 108 (shown in FIG. 1) and into the body cavity. In some embodiments, a sleeve (not shown, but readily understood as a lining layer) may be located within the cannula 106, and the scope 132 may pass through the sleeve. Once deployed, the scope 132 may be manipulated by the medical professional moving it distally/proximally, angling it, and/or by rotating it into a particular orientation. Typically, during laparoscopic procedures, scopes can become obstructed when debris (e.g., condensation, displaced tissue, bodily fluids) are encountered and accumulate on a lens of the scope, which may compromise the image or video feed provided to the medical professional.

As shown in FIG. 2, the trocar assembly 102 may include the cleaning element 136 forming a surface 138 at a location within the internal environment. The housing 104 may include a cleaning element receiving surface 135 configured (e.g., sized and shaped) to receive, and attach to, the cleaning element 136. The cleaning element may have a surface (such as the bottom surface 129) configured to secure to the cleaning element receiving surface 135. For example, the bottom surface 129 may have an adhesive or other tacky/sticky substance to adhere to the cleaning element receiving surface 135, but additional and/or alternative securement devices are contemplated. The surface 138 of the cleaning element 136 may facilitate removal of obstructions from the scope 132 without necessitating removal of the scope 132 from the internal environment. Advantageously, lengthy interruptions (and therefore increased surgical and anesthesia time) due to removing and/or replacing an obstructed scope may be reduced or eliminated. Further, the distal end of the scope 132 may remain in the sterile internal environment during cleaning, which may advantageously alleviate concerns related to loss of sterility within the internal environment due to the removal and re-entry of the scope 132 one or more times for cleaning purposes. Keeping the scope 132 within the internal environment may also reduce or eliminate debris in the form of fogging or condensation caused by exposure to pressure and/or temperature changes when switching between environments. It should also be understood that certain advantages of the present embodiments are generally described as relating to a scope for explanation purposes and may also extend to other types of instruments used during surgical procedures, and therefore "scope" should be understood as including any suitable medical device used during laparoscopic surgery when described in the context of the present embodiments, unless clearly excluded.

The cleaning element 136 may incorporate any suitable structures, materials, and/or cleaning solutions for moving obstructions from the scope 132. The cleaning element may have a unitary construction, or alternatively may have multiple surfaces or layers with different cleaning characteristics or properties for facilitating multiple treatments. For example, it is contemplated that the cleaning element 136 may have a first region with an abrasive surface for breaking up potential obstructions, a second region including a liquid, a gel, or other material for dissolving or washing away the obstructions, and a third region with an absorbent or adsorbent surface for removing any remaining residue.

The cleaning element 136 may include any suitable cleaning structures or materials, such as sponges, foams (e.g., reticulated or non-reticulated foamed plastic polymers forming open-cell, semi-open cell, or closed-cell foam structures), fibrous materials (e.g., materials with natural (e.g., cellulosic) and/or synthetic fibers), microfiber or wipe materials (e.g., polyethers, polyamides, polyesters, and/or blends of each in a woven or non-woven construction with split or non-split fibers), hydrophilic or hydrophobic materials, fluids, gases, bristles, films, etc. The structures and/or materials of the cleaning element 136 may include and hydrophobic properties to assist in absorbing and wicking of various bodily fluids and/or lipophilic characteristics for increased absorption of oils or fats. The cleaning element 136 may be capable of absorbing at least 5 times its original weight of fluids, such as about 15 times its original weight (or more). When the cleaning element 136 includes pores, consistent or variable pore sizes may be consistently or randomly dispersed (or layered) in certain configurations for suitable absorption properties (for example, a the cleaning element 136 may include a micro-porous foam with about 4 pores per inch to about 100 pores per inch). The cleaning element 136 may have a firmness/compliance of about 2 lbs/50 in$^2$ to about 80 lbs/50 in$^2$, and preferably about 6 lbs/50 in$^2$ to about 45 lbs/50 in$^2$ (when tested at 25% deflection on a 20 inch by 20 inch by 4 inch specimen). The material(s) of the cleaning element 136 may be formed of a material suitable for use in a medical device (e.g., with suitable biocompatibility, non-linting/no particulate, tear resistance, sterilization or other chemical/solvent compatibility, and radiation stability).

The cleaning element 136 may be multi-layered in some embodiments. For example, a first layer may be configured to absorb a fluid obstruction located on the scope 132, and a second layer may be configured to retain or discard that fluid. In some embodiments, the first layer may include an open-cell foam with relatively low density (such as polyurethane or silicone foam) that may be used to effectively and quickly absorb (or wick, etc.) the obstructing fluid, and the second layer may include higher-density foam for effectively retaining the fluid. The second layer may be located beneath (e.g., covered by) the first layer, for example. Fibrous materials such as terrycloth and microfiber cloths may additionally or alternatively be used and may be advantageous for providing a streak-free lens surface when wiped against the scope 132. The solid materials of the cleaning element 136 may be combined or "wetted" with a cleaning fluid, such as an anti-fog fluid, sterile water, saline, a detergent, etc, which may facilitate the removal of fatty smudges and dried-on debris.

Referring to the trocar assembly 102 of FIG. 2, in the event the medical professional's visibility becomes compromised due to obstruction of the scope 132 during surgery, the scope 132 may be retracted proximally such that the distal end of the scope 132 is located within the chamber 120. The distal end 134 (or other location) may then be wiped or swept by pressing and/or rubbing the distal end 134 of the scope 132 on the cleaning element 136 to remove obstructions. As explained above, this cleaning procedure may advantageously be completed without removing the scope 132 from the internal environment in the trocar assembly 102. In some embodiment, the housing 104 may be formed of a transparent or translucent material such that a user has a visual perspective of the cleaning element 136, the scope 132, and other objects in the chamber 120 during the cleaning procedure. Similarly, the cannula 106 may be formed of a transparent or translucent material. When the scope 132 is located in the trocar assembly 102, the scope 132 (which often includes a light) may illuminate the chamber 120 to increase visibility, even if the housing 104 is not fully transparent. While the housing 104 may be fully formed of a transparent or translucent material, the housing 104 may alternatively include an opaque material and also include at least one viewport formed of transparent or translucent material.

In some embodiments, the cleaning element 136 may be selectable, removable, and/or replaceable. Thus, the trocar assembly 102 may be capable of allowing access into the chamber 120 (e.g., in an operating room prior to a surgery) such that a medical professional can select an appropriate version of the cleaning element 136 and then use that cleaning element 136 with the trocar assembly 102 during the procedure. The access may be provided by separating an upper portion 190 of the housing from a lower portion 192 of the housing, for example. The cleaning element 136 may additionally or alternatively be replaced during a medical procedure (e.g., if it becomes soiled), and/or may be replaced between medical procedures during reprocessing of the trocar assembly 102 if the trocar assembly 102 is reusable.

After completion of the cleaning procedure, the distal end 134 of the scope 132 may be again advanced through the cannula 106 and out beyond the cannula distal end to restore the image or video feed provided by the scope. Those of skill in the art will appreciate that existing scopes and potential scope designs include at least one non-longitudinal, distal-end-facing surface of the distal end 134 that may be generally or exactly perpendicular to the longitudinal axis of the scope 132, or which distal-facing surface may be configured at a non-perpendicular angle relative to the longitudinal axis (e.g., 30 degrees off-perpendicular, 45 degrees off-perpendicular). It is further contemplated that the distal-facing surface of the scope 132 may be flat/planar, concave, or convex relative to the major plane of that face. The term "non-longitudinal, distal-end-facing surface" is meant to include the operative end face(s) of a scope in distinction from the longitudinal lateral sides of the scope, which will generally be columnar cylindrical. Thus, as described in more detail below, the surface characteristics of the cleaning element 136 may be shaped or otherwise configured for compatibility with a variety of distal-facing surfaces of the scope 132.

Figure 3:
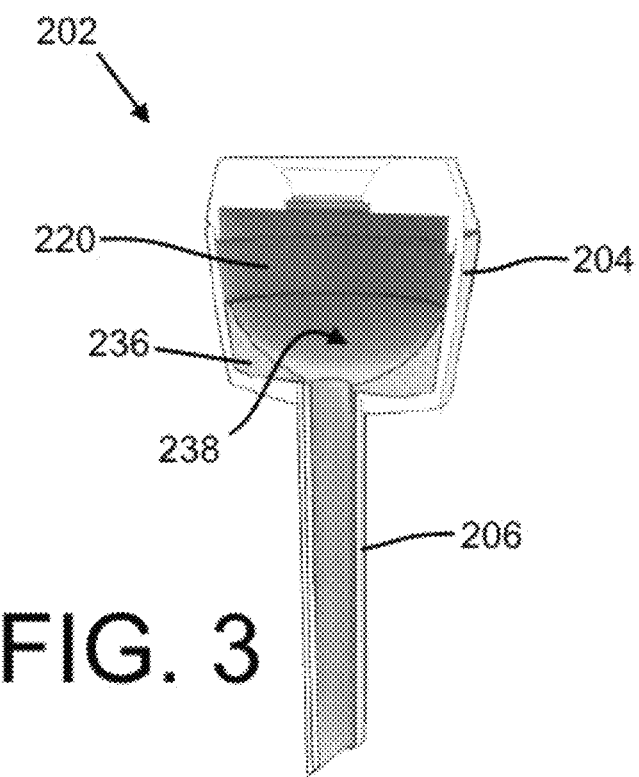
FIG. 3 shows another embodiment of a trocar assembly with a curved convex cleaning surface and lined cannula in accordance with the present disclosure.

FIG. 3 shows a trocar assembly 202 with a housing 204, a chamber 220, and a cannula 206. The trocar assembly 202 includes a cleaning element 236 with a concave surface 238 (or other curved surface) within the chamber 220. The concave surface 238 may be advantageous for providing a cleaning profile that matches a profile of a scope with a distal non-perpendicular face, such as a curved (e.g., convex) or angled lens, or other curved instrument, for example. The concave surface 238 may advantageously increase the total surface area of the cleaning element 236 when compared to a flat cleaning element, which may be advantageous when more than one cleaning procedure will take place without replacing or reprocessing the trocar assembly 202, particularly if previously-used areas of the cleaning element 236 cannot be reused without reprocessing (e.g., due to buildup of debris).

The cleaning element 236 may also line the cannula 206 or otherwise extend through the cannula 206, as depicted by FIG. 3. Advantageously, this embodiment may provide the ability to clean a scope while retracting it through the cannula 206 and/or without necessitating retraction of the distal end 234 of the scope the entire way to the chamber 220, particularly when the obstructed instrumentation is located on an outer-diameter surface along the elongated body of the scope. The cleaning element 236 may extend all the way to the distal end of the cannula 206, or not. While not shown, it is contemplated that the entirety of the inner surface area of the trocar assembly 202 within the internal environment may include one or more cleaning element(s) 236.

Figure 3A:
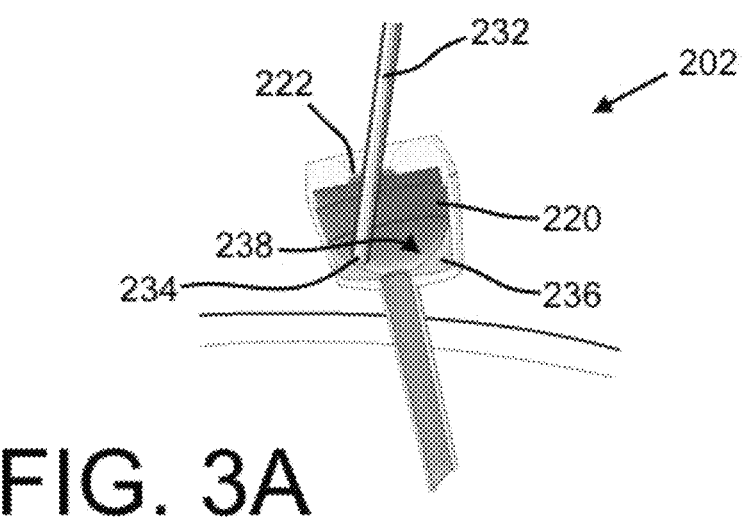
FIG. 3A shows the trocar assembly of FIG. 3 during a cleaning procedure in accordance with the present disclosure.

FIG. 3A shows the embodiment of the trocar assembly 202 of FIG. 3 during a cleaning procedure in accordance with the present disclosure. As shown, the scope 232 may be received into the chamber 220 of the housing 204 through the top opening 222. While not shown, a valve may be located at the top opening 222 to form a fluid barrier at the top opening 222, thereby sealing the environment inside the chamber 220 from an external environment. The cleaning element 236 may include the curved concave surface 238, which is particularly advantageous when the scope 232 has angled distal end 234 as depicted, a curved distal end, or another non-planar distal end. To clean the distal end 234 of the scope 232, the user may wipe the distal end 234 of the scope 232 against the concave surface 238 of the cleaning element 236 to remove debris. At least a portion of the cleaning element 236 may be relatively compliant such that when the user presses the distal end of the scope 232 against the cleaning element 236 with sufficient force, the contact portion of the cleaning element 236 yields and at least partially assumes the shape of the distal end 234 of the scope 232 to thereby provide a larger surface area of contact.

Figure 4:
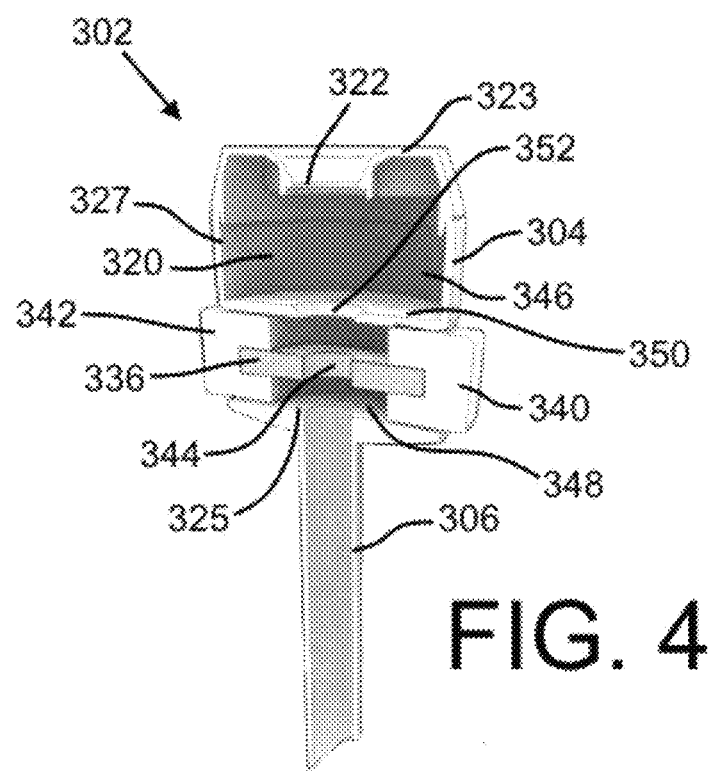
FIG. 4 shows a trocar assembly with movable buttons for displacing a cleaning element in response to an input force in accordance with the present disclosure.

Another embodiment of a trocar assembly 302 is depicted in FIG. 4. Like other embodiments described herein, the trocar assembly 302 includes a housing 304 with a chamber 320 and a cannula 306 extending from the chamber 320. A proximal or top wall 323 of the housing 304 may include an opening 322, which may be configured to receive a scope and which may be associated with a valve (not shown) for sealing the chamber 320 from an external environment. The chamber 320 may be defined by the top wall 323, a distal or bottom wall 325, and a generally cylindrical side wall 327 extending from the top wall 323 to the bottom wall 325. The housing 304 includes a first button 340 and a second button 342. Herein, a "button" may be a structure that moves in response to an input force applied by a user. The buttons 340, 342 may form a portion of the side wall 327 such that the chamber 320 is deformable (e.g., inwardly). The first button 340 and the second button 342 are secured to a cleaning element 336 such that movement of the first button 340 and/or the second button 342 effects displacement of the cleaning element 336. The buttons 340, 342 may be configured to move in response to an input force applied to one or more of the buttons 340, 342. So, the cleaning element 336 may displace from a default state (shown in FIG. 4) to a displaced state (not shown) when one of the buttons 340, 342 is moved in response to the applied input force. The input force may result from a medical professional intentionally applying pressure on one of the buttons 340, 342, for example. While two buttons are depicted, more or fewer than two buttons may be included. The buttons may be coupled to a spring or other biasing element such that the cleaning element 336 returns to the default state when the input force is removed from the buttons 340, 342. It is contemplated that the resiliency of the cleaning element 336 may provide the biasing/spring force, particularly when the cleaning element 336 includes a resilient material, such as a particular foam, rubber, or plastic. Therefore, the cleaning element 336 may include a tendency to assume the default state in the absence of an input force (shown, in the non-limiting illustration of FIG. 4 as a flat circular disc with a center-hole, but able to be embodied differently within the scope of the present disclosure).

The cleaning element 336 may have an opening 344 to provide access from a proximal portion 346 of the chamber 320 to a distal portion 348 of the chamber, and/or from the proximal portion 346 of the chamber 320 to the cannula 306. The opening 344 may be aligned with a longitudinal axis of the cannula 306 such that substantially straight elongated instruments extending through the cannula 306 also may extend proximally through the opening 344. The diameter (or other cross-sectional dimension) of the opening 344 may be approximately equal to, or slightly larger than, the inner diameter of the cannula 306 and/or an outer diameter of a scope, which may be advantageous for allowing the scope to pass through the opening 344 without catching or creating friction when being manipulated during the laparoscopic procedure. Alternatively, it may be advantageous for the diameter of the opening 344 to be less than the diameter of certain instruments (and therefore less than the inner diameter of the cannula 306) such that the cleaning element 336 contacts the outer diameter of those instruments, thereby cleaning the outer diameter surface of those instruments and/or providing a friction to give a medical professional precise control, including a braking-like control, of the distal/proximal movement and rotation of that instrument.

In some embodiments, the opening 344 allows certain instruments, such as a scope, access to the cannula 306 when the cleaning element 336 is in the default state, and then restricts access to the cannula 306 when the cleaning element is in the displaced state. Advantageously, when the scope becomes obstructed by debris, the scope may be withdrawn proximally through the opening 344 such that a distal end of the scope is within the proximal portion 346 of the chamber 320. Then, the cleaning element 336 may be displaced as a result of an input force applied to one or more buttons, as described above. The displacement of the cleaning element 336 may change the location and/or the dimensions of the opening 344 such that when the scope is advanced distally towards the cannula 306, it does not proceed through the opening 344 but instead contacts the cleaning element 336. Accordingly, the scope may contact the cleaning element 336 for cleaning purposes. After cleaning, the input force may be removed from the buttons, the cleaning element 336 may then return to the default state providing access to the cannula 306 through the opening 344, and the scope may then be advanced distally through the cannula 306 to again resume its function inside the body cavity.

While not required, the housing 304 may include a divider 350 separating the proximal portion 346 of the chamber 320 from the distal portion 348 of the chamber 320. The divider 350 may provide suitable support and guidance for the buttons 340, 342, for example. The divider 350 may include a guide opening 352, which may retain the distal end of the scope such that it remains approximately aligned with the cannula 306 during the cleaning process. This may facilitate efficient re-entry into the cannula 306 after cleaning. While not required, the opening 352 of the divider 350 may include a valve or other suitable device for creating a seal between the distal portion 348 of the chamber 320 and the proximal portion 346 of the chamber 320. In other embodiments, the distal portion 348 of the chamber 320 may be in fluid communication with the proximal portion 346 of the chamber 320, which may be advantageous for eliminating or reducing pressure and/or temperature change when a distal end of a scope is moved between chamber portions. The divider 350 is not required in all embodiments.

Figure 5:
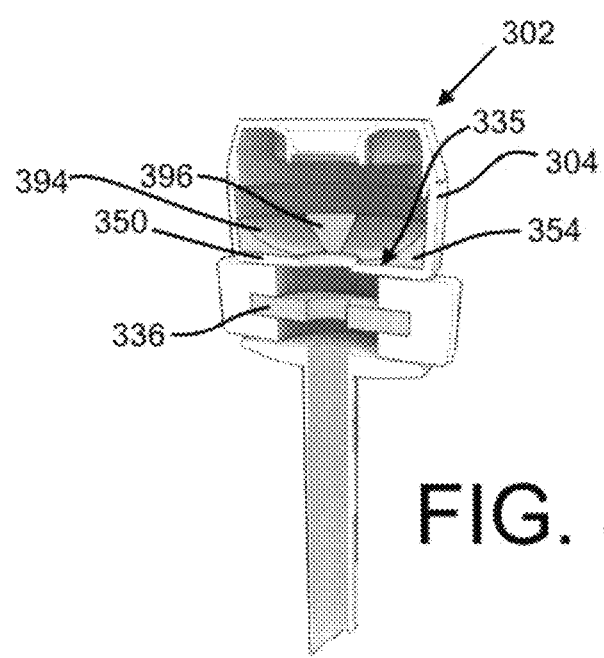
FIG. 5 shows the trocar assembly of FIG. 4 with a second cleaning element in accordance with the present disclosure.

As shown an embodiment illustrated in FIG. 5, the divider 350 may include cleaning element receiving surface 335 configured (e.g., sized and shaped) to receive and attach to a second cleaning element 354. The second cleaning element 354 may include one or more of the features of at least one of the cleaning elements described above with respect to FIG. 2 and FIG. 3. The two cleaning elements 336, 354 may be intended for different degrees of debris removal, or may otherwise have at least one different cleaning property. For example, it is contemplated that more efficient, but potentially less effective cleaning may be performed with the cleaning element 336, while more extensive cleaning may be carried out by the second cleaning element 354 (e.g., "rough cleaning" and "fine cleaning," respectively, analogous in such an example to a coarse filter for removing larger elements, and fine filter for polishing and removing smaller elements). Further, the first cleaning element 336 may be better suited for debris removal on side surfaces of a scope, while the second cleaning element 354 may be better suited for removing debris on a distal-face surface.

It is also contemplated that a single cleaning element may have two surface-area portions that are configured differently (i.e., have at least one different cleaning property). For example, a first surface area portion 394 of the second cleaning element 354 may be configured for cleaning without a cleaning fluid, and a second surface area portion 396 may be wetted or may otherwise be configured for a different cleaning function than the first surface area portion 394. The two surface area portions may have different colors or other visual characteristics such that a user can readily distinguish between the surface area portions visually (particularly when the housing 304 is transparent or translucent). Alternatively (or in addition), the scope may provide visual feedback to an external screen or other device to facilitate distinguishing between surface area portions. It is also contemplated that the surface area portions may have different textures or otherwise provide a tactical indication that a user can sense when rubbing or otherwise contacting a scope with the surface area portions, which may be advantageous for ensuring completion of the proper cleaning function(s).

Figure 6:
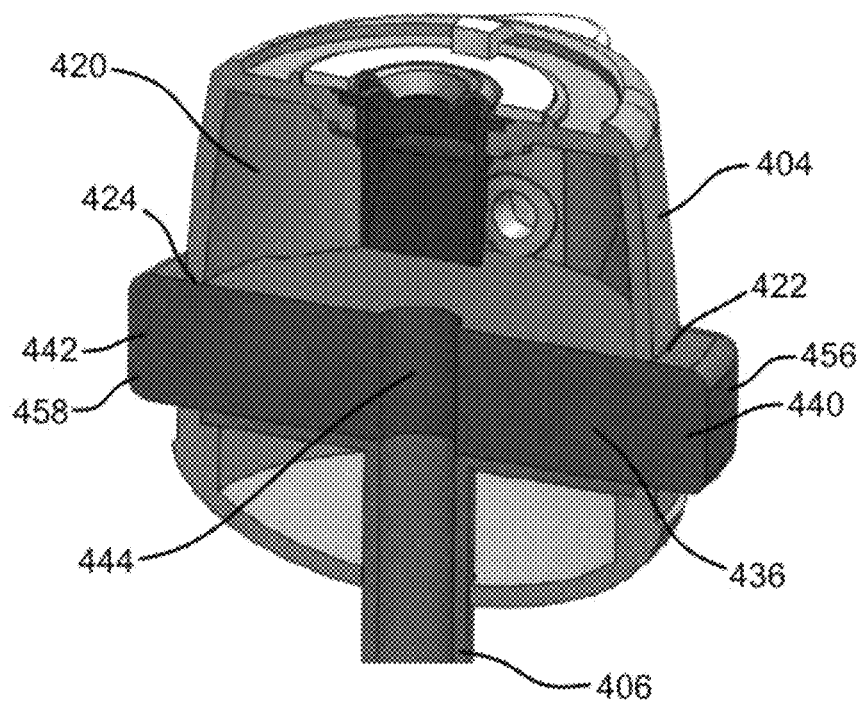
FIG. 6 shows another embodiment of a trocar assembly having a cleaning element with portions extending to a location outside of a housing in accordance with the present disclosure.

FIG. 6 shows a trocar assembly 402 with a cleaning element 436 having a first portion 456 and a second portion 458 extending to a location outside of a housing 404. The first portion 456 and the second portion 458 of the cleaning element 436 may respectively form a first button 440 and a second button 442 for receiving an input force. The first portion 456 and the second portion 458 may form a portion of the shell of the housing 404 that defines the chamber 420 and retains a pressure differential between the chamber 420 and the external environment. The cleaning element 436 may further include an opening 444 providing access to a cannula 406 at least when the cleaning element 436 is in a default state. Similar to as described above with reference to FIG. 4 and FIG. 5, that access may be restricted when an input force is applied to at least one of the first button 440 and the second button 442, thereby moving the cleaning element 436 and the opening 444 into a displaced state. Natural resiliency of a material forming the cleaning element 436 may ensure the cleaning element 436 is in the default state when no input force is provided. The portions of the cleaning element 436 forming the first button 440 and/or the second button 442 may include a compressible/compliant material slightly larger (when/where not compressed) than corresponding openings 422, 424 of the housing 404, which may advantageously retain a fluid barrier between the chamber and an external environment by contacting the chamber in a sealing/compliant manner (when still and when being moved/displaced) so as to prevent or at least inhibit loss of fluid from the chamber 420 (e.g., positive insufflation pressure, liquids from cleaning and/or medical procedures).

Figure 7:
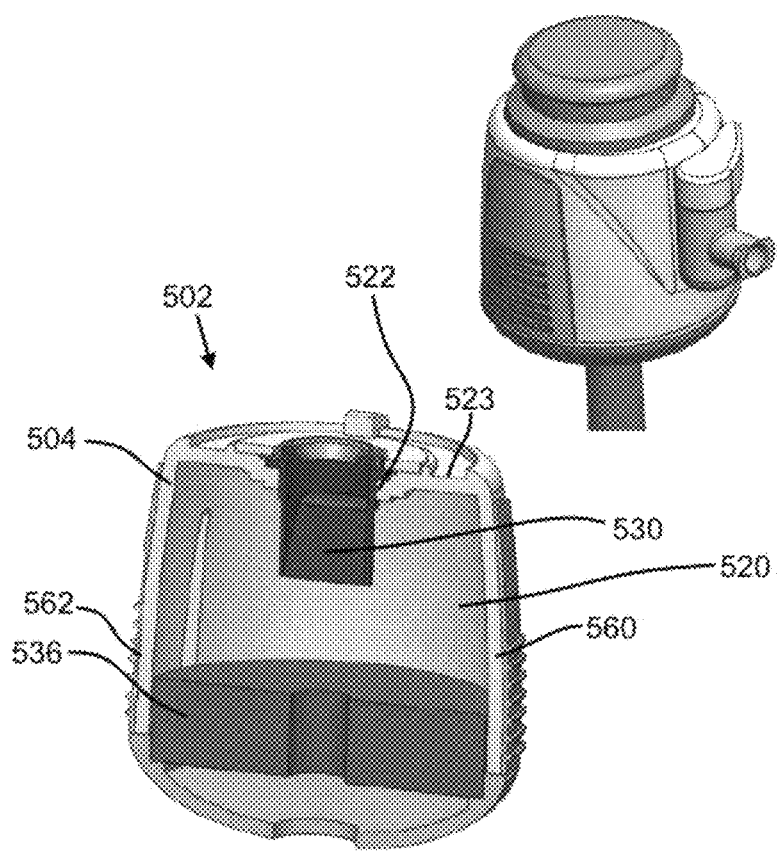
FIG. 7 shows another embodiment of a trocar assembly with a housing having flexible wall portions in accordance with the present disclosure.

Another embodiment of a trocar assembly 502 is shown in FIG. 7. The trocar assembly 502 may include a housing 504 and a cleaning element 536 forming a cleaning surface within the housing 504, as shown. As in certain embodiments described above, the housing 504 may form a chamber 520 that is sealed from an external environment. A scope or other medical device may be received by the trocar assembly 502 through a top wall 523 of the housing 504, and specifically through an opening 522 of the top wall 523 of the housing 504. A valve 530 may form a fluid-barrier around an outer surface of the scope to retain the seal between the chamber 520 and the external environment when the scope is received by the trocar assembly 502. The housing 504 may include one or more flexible wall portions 560, 562, which may act as (and be referred to) as buttons for receiving an input force. The input force may cause the flexible wall portions 560, 562 to flex, thereby forcing the cleaning element 536 from the depicted default state to a displaced state. The resiliency of the flexible wall portions 560, 562 and/or the resiliency of the cleaning element 536 may cause movement back to the default state when the input force is removed.

Similarly, a trocar assembly 602 depicted in FIG. 8 has a first flexible wall portion 660 and a second flexible wall portion 662. Here, the first flexible wall portion 660 and the second flexible wall portion 662 are formed by openings 664, 666 within an outer shell 668 of the housing 604, where a cleaning element 636 at least partially forms an inner shell 670 of the housing 604. It is contemplated that the inner shell 670 may be formed entirely by the cleaning element 636. The inner shell 670 may cover the openings 664, 666 such that a fluid barrier between a chamber 620 of the housing 604 and the external environment is not compromised. As shown, the inner shell 670 may form at least a portion of an external surface of the housing 604, and may be substantially surrounded by the outer shell 668.

When a scope is located in the chamber 620, an input force may be applied to at least one of the first flexible wall portion 660 and the second flexible wall portion 662 such that the cleaning element 636 deflects towards the center of the chamber for easier and more comprehensive cleaning of the scope. Further, when the inner shell 670 is relatively thin and compliant, this embodiment may be advantageous for providing a medical professional with a sense of feel (i.e., tactile indication) with respect to the scope by allowing the medical professional to indirectly touch the scope (through the inner shell 670), which may provide for efficient and effective wiping or sweeping of debris from the scope. While not shown in FIG. 8, a second cleaning element may be included on another surface of the chamber 620 (e.g., a bottom or distal surface, which may be a cleaning element receiving surface), which may have features described in certain embodiments above with reference to FIG. 4 and FIG. 5, for example.

FIG. 8A shows a second illustration of the embodiment of the trocar assembly 602 of FIG. 8 (but also with an insufflation inlet 628). As shown, the outer shell 668 may include the opening 664, and the cleaning element 636 (and particularly the flexible wall portion 660, shown as partially transparent in FIG. 8A) may be aligned with the opening 664 such that it is accessible by a user and such that a user can press the flexible wall portion 660 by reaching/pressing through the opening 664. The cleaning element 636 may also cover the opening 664 and function as seal or fluid barrier between the chamber 620 and the external environment. Thus, the cleaning element 636 may include a material that is not permeable or is substantially impermeable by air or other gasses/fluids. It is contemplated that only an outer layer or portion of the cleaning element 636 forms the seal, while an inner layer or portion is configured for absorption and retention of a liquid or other fluid (as described in more detail above). Additionally or alternatively, a fluid-impermeable cover or other element may be placed on the cleaning element 636 and over the opening 664 for forming the seal between the chamber 620 and the external environment.

Figure 9:
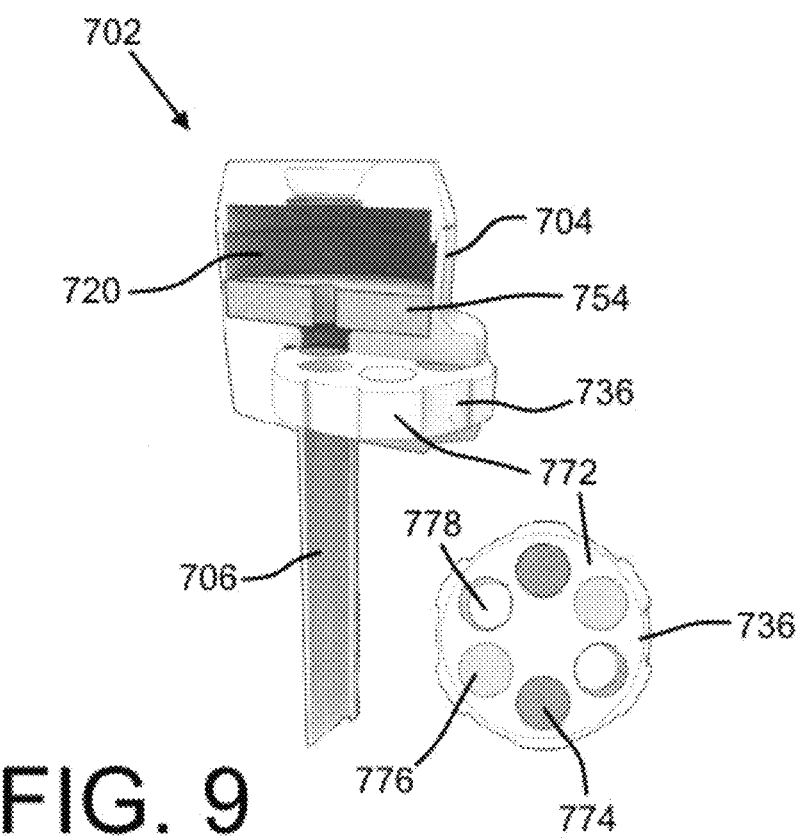
FIG. 9 shows another embodiment of a trocar assembly with an adjustable cleaning element in accordance with the present disclosure.

FIG. 9 shows a trocar assembly 702 with an adjustable cleaning element 736 and a second cleaning element 754. The second cleaning element 754 may form a surface within a chamber 720 of the housing 704 and may be similar to the cleaning element 136 of FIG. 2, for example. The adjustable cleaning element 736 may be configured to rotate, slide, or otherwise move to adjust its position and/or orientation relative to the housing 704. In the depicted embodiment, the adjustable cleaning element 736 includes a wheel 772 with a pair of first cleaning surfaces 774, a pair of second cleaning surfaces 776, and a pair of openings 778. Alternatively, more or fewer than two types of cleaning surfaces may be included. When in a first setting (depicted), the cleaning element 736 may restrict access to a cannula, and the first cleaning surface 774 may be located along a longitudinal axis of the cannula 706 such that a scope will contact the first cleaning surface 774 when moving distally within the chamber 720 and towards the cannula 706. The first cleaning surface 774 may include certain surface characteristics and/or incorporate a cleaning material (e.g., a cleaning liquid) for carrying out a first cleaning treatment. For example, the first cleaning surface 774 may include a cleaning liquid or other fluid that may dissolve and loosen debris from the scope.

Next, the cleaning element 736 may be rotated to a second setting such that the second cleaning surface 776 is positioned to contact the scope. The second cleaning surface 776 may include certain surface characteristics and/or materials for carrying out a second cleaning treatment. For example, the second cleaning surface 776 may include an abrasive and/or absorbent surface that removes debris and absorbs residue (which is also considered debris herein) that remain on the scope after the first cleaning step. In this example, the two cleaning steps can be repeated as necessary by rotating the cleaning element 736 and repeating contact between particular cleaning surfaces and the scope. A cleaning surface may additionally or alternatively include a rubber or other material suitable for squeegeeing or otherwise wiping away fluid debris from a lens.

When the cleaning processes are complete, the cleaning element 736 may be rotated or otherwise moved to a third setting such that the opening 778 is aligned with the cannula 706 to provide the scope with access to the cannula 706. The opening 778 is depicted as a round hole in FIG. 9, but other suitable openings are contemplated (e.g., a wedge or pie-shaped or other-shaped gap in the wheel 772, a hole of a different shape, etc.). The cleaning element 736 may include openings of different shapes and sizes (and also cleaning surfaces of different shapes and sizes) for compatibility with multiple types of scopes and other medical instruments. It is contemplated, for example, that certain cleaning surfaces of the movable cleaning element 736 are concave in shape for interaction with a convex instrument surface, while others are flat for interaction with a flat instrument surface.

Figure 10:
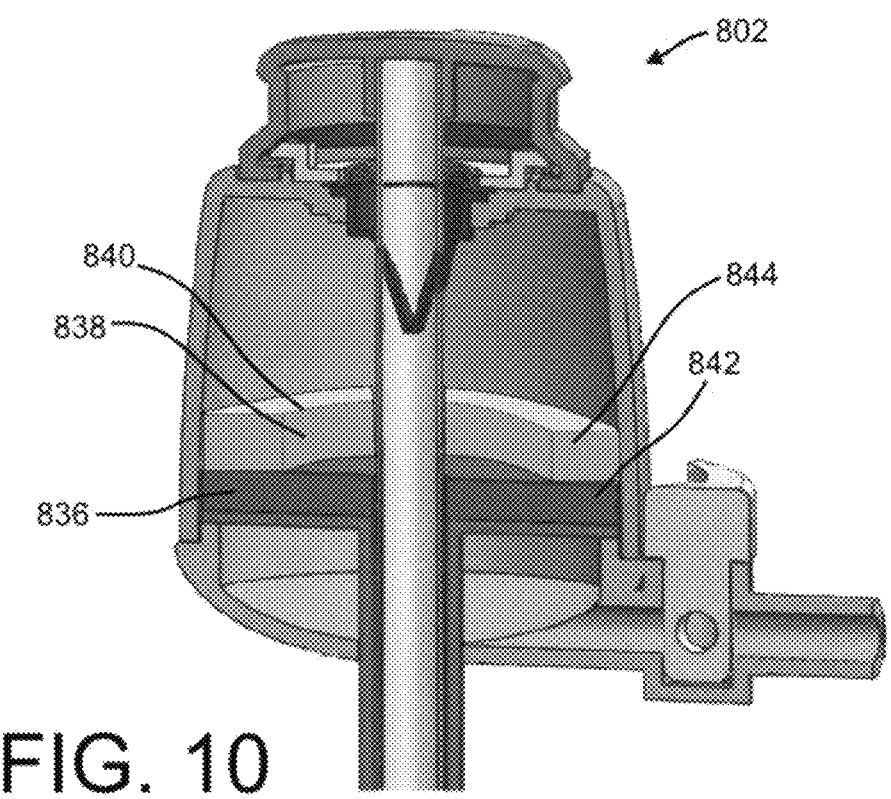
FIG. 10 shows another embodiment of a trocar assembly with disclosure cleaning element having two disk portions.

FIG. 10 shows a trocar assembly 802 similar to the trocar assembly 202 of FIG. 2, but with a different embodiment of a cleaning element 836. As shown in FIG. 10, the cleaning element 836 may include a stepped portion 838. Advantageously, during a cleaning procedure, the stepped portion 838 may provide an edge 840 (which may be a sharp corner or a rounded edge) that can be used as a scraping edge and/or that can be used to ensure suitable contact of a scope with an angled lens, for example. The stepped portion 838 may be formed by including two portions of the cleaning element 836: a first disk portion 842 and a second disk portion 844, where the second disk portion 844 is located on a proximal surface of the first disk portion 842, and where the second disk portion 844 has a larger inner diameter than the first disk portion 842 such that the proximal surface of the first disk portion 842 remains accessible. Alternative constructions are also contemplated for forming the stepped portion 838. In one non-limiting example, the cleaning element 836 may include an outer disk with a first height and an inner disk with a second height, where the first height is greater than the second height, and wherein an inner diameter of the outer disk surrounds an inner diameter of the second disk (i.e., such that the second disk is "inside" the first disk). A cleaning element 836 with a stepped portion may be included in any of the embodiments of trocar assemblies described above. Cleaning elements with other surface characteristics are also contemplated. For example, a cleaning surface may be flat (e.g., as in FIG. 2), curved concavely (e.g., as in FIG. 3), curved convexly, stepped (e.g., as in FIG. 10), sloped or angled, wavy, spiked, etc.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. This specifically includes that the structure, location, and mechanisms of the disclosed cleaning elements and related structures in the different embodiments illustrated and described with reference to the drawing figures may be combined and elements interchanged within the level of skill in the art as informed by this application, and within the scope of the present claims, which includes that a variety of disclosed individual cleaning element components dimensioned for use encompassed within in laparoscopy trocars may be configured as separable/replaceable components of a larger trocar assembly. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:
1. A trocar assembly with an integrated scope-cleaning structure, the trocar assembly comprising:
   a chamber with a proximal opening configured to receive a distal end of a scope, wherein the chamber has a first diameter;

a cannula extending distally from the chamber, and configured to extend distally into a patient body, wherein the cannula is further configured to receive the distal end of the scope such that the scope can be maneuvered through the cannula to a location within the patient body, wherein the cannula has a second diameter, and wherein the first diameter is larger than the second diameter; and a cleaning element forming a surface within the chamber, wherein the surface of the cleaning element is configured to remove debris from at least one non-longitudinal, end-facing surface of the scope.

2. The trocar assembly of claim 1, further comprising a valve configured to form a fluid barrier at or near the proximal opening between an environment within the chamber and an external environment.

3. The trocar assembly of claim 1, wherein cleaning element includes an opening aligned with a longitudinal axis of the cannula.

4. The trocar assembly of claim 1, wherein the surface of the cleaning element includes a curved portion.

5. The trocar assembly of claim 1, wherein the cleaning element is movable with respect to the chamber in response to an input force between a default state and a displaced state.

6. The trocar assembly of claim 5, wherein the cleaning element includes an opening, wherein a longitudinal axis of the cannula extends through the opening when the cleaning element is in a default state, and wherein the cleaning element at least partially obstructs the cannula from a proximal viewpoint when the cleaning element is in a displaced state.

7. The trocar assembly of claim 5, further comprising a button coupled to the cleaning element, wherein the input force is applied to the button, and wherein the button is movable with respect to the chamber in response to the input force.

8. The trocar assembly of claim 1, wherein at least a portion of the cleaning element extends along an inner diameter surface of the cannula.

9. The trocar assembly of claim 1, wherein the cleaning element includes a stepped portion with an edge.

10. A trocar assembly for use during a laparoscopic procedure, the trocar assembly comprising:
a housing forming a chamber, the chamber having a proximal opening configured to receive a distal end of a scope;
a cannula extending distally along a longitudinal axis from the housing and configured to extend distally into a patient body, wherein the cannula is further configured to receive the distal end of the scope such that the scope can be maneuvered through the cannula to a location within the patient body; and
a cleaning element receiving surface disposed within the chamber at a proximal end of the cannula, wherein the cleaning element receiving surface is configured to receive a cleaning element with a cleaning surface for removing debris from at least one non-longitudinal, end-facing surface of the scope.

11. The trocar assembly of claim 10, further comprising a valve configured to form a fluid barrier at the proximal opening between an environment within the chamber and an external environment.

12. The trocar assembly of claim 10, wherein the cleaning surface includes an opening aligned with the longitudinal axis of the cannula when the cleaning surface is received by the cleaning element receiving surface.

13. The trocar assembly of claim 10, wherein the surface of the cleaning element includes a curved portion.

14. The trocar assembly of claim 10, wherein the cleaning element is movable with respect to the housing in response to an input force between a default state and a displaced state.

15. The trocar assembly of claim 14, wherein the cleaning element includes an opening, wherein a longitudinal axis of the cannula extends through the opening when the cleaning element is in a default state, and wherein the cleaning element at least partially obstructs the cannula from a proximal viewpoint when the cleaning element is in a displaced state.

16. The trocar assembly of claim 14, further comprising a button coupled to the cleaning element, wherein the input force is applied to the button, and wherein the button is movable with respect to the chamber in response to the input force.

17. The trocar assembly of claim 10, wherein the cleaning element includes a stepped portion with an edge.

18. A cleaning element for cleaning at least one surface of a scope while that scope is engaged into a trocar assembly, the cleaning element comprising:
at least one absorbent cleaning surface configured to remove debris from at least one non-longitudinal, end-facing surface of a scope; and
a second surface configured to secure to a cleaning element receiving surface within a chamber of a trocar assembly,
wherein the cleaning surface of the cleaning element is configured to be fully encompassed within a chamber of a trocar assembly during a cleaning procedure, and
wherein the cleaning element forms an opening that has a diameter at least as large as a diameter of a cannula leading to a distal end of the trocar assembly such that the opening provides access to the cannula when the cleaning element is secured to the cleaning element receiving surface.

19. The cleaning element of claim 18, wherein the at least one absorbent cleaning surface includes at least one of a concave portion and a stepped portion.

20. The cleaning element of claim 18, wherein at least a portion of the cleaning surface is displaceable from a default state to a displaced state in response to an input force applied to the cleaning element.

* * * * *